(12) United States Patent
Mueller et al.

(10) Patent No.: US 7,588,554 B2
(45) Date of Patent: Sep. 15, 2009

(54) METHOD AND APPARATUS FOR TREATING ISCHEMIC TISSUE (75) Inventors: Richard L. Mueller, Byron, CA (US); U. Hiram Chee, Santa Cruz, CA (US); James R. Kermode, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 09/891,715

(22) Filed: Jun. 26, 2001

(65) Prior Publication Data

US 2002/0072717 A1 Jun. 13, 2002

Related U.S. Application Data (60) Provisional application No. 60/214,053, filed on Jun. 26, 2000.

(51) Int. Cl.
*A61M 31/00* (2006.01)
(52) U.S. Cl. .................... 604/93.01; 604/21
(58) Field of Classification Search ........... 604/20–22, 604/506, 95.01, 95.05, 95.04, 158, 264, 523, 604/164.01, 93.01; 600/129, 130, 131, 139, 600/146, 149; 606/167; 607/50, 2, 99, 101, 607/115–120, 123
See application file for complete search history.

(56) References Cited

U.S. PATENT DOCUMENTS 3,773,034 A 11/1973 Burns et al.
3,797,491 A 3/1974 Hurschman
3,952,742 A 4/1976 Taylor
4,222,380 A 9/1980 Terayama
4,243,035 A 1/1981 Barrett
4,296,100 A 10/1981 Franco
4,531,936 A 7/1985 Gordon
4,578,061 A 3/1986 Lemelson
4,657,536 A 4/1987 Dorman (Continued)

FOREIGN PATENT DOCUMENTS

WO   WO 96/32129   10/1996

(Continued)

OTHER PUBLICATIONS

Simon Carrette et al., "Epidural Corticosteroid Injections For Sciatica Due To Herniated Nucleous Pulposus", Jun. 5, 1997, The New England Journal of Medicine, vol. 336, No. 23, pp. 1634-1640.*

(Continued)

*Primary Examiner*—Nicholas D Lucchesi
*Assistant Examiner*—Theodore J Stigell
(74) *Attorney, Agent, or Firm*—Crompton, Seager & Tufte LLC (57) ABSTRACT The invention described herein provides for methods and devices for treating tissues, and in particular, ischemic heart tissue. Preferred devices includes tools integrating both injury and treatment effectors in a single unit. An optional third effector provides an effector for marking locations on a tissue surface that have been visited by the device. Methods are provided in which a target tissue is identified, injury sites are created at known locations, and therapeutic-substance is infused at known locations different than the injury sites.

20 Claims, 10 Drawing Sheets

U.S. PATENT DOCUMENTS

| | | | |
|---|---|---|---|
| 4,770,653 A | 9/1988 | Shturman | |
| 4,911,148 A | 3/1990 | Sosnowski et al. | |
| 4,946,442 A | 8/1990 | Sanagi | |
| 4,994,033 A | 2/1991 | Shockey et al. | |
| 5,034,003 A | 7/1991 | Denance | |
| 5,061,223 A | 10/1991 | Yock | |
| 5,106,370 A | 4/1992 | Stewart | |
| 5,185,004 A | 2/1993 | Lashinski | |
| 5,203,772 A | 4/1993 | Hammerslag et al. | |
| 5,244,460 A | 9/1993 | Unger et al. | |
| 5,322,511 A | 6/1994 | Armbruster et al. | |
| 5,380,279 A | 1/1995 | Schmidt | |
| 5,385,148 A | 1/1995 | Lesh et al. | |
| 5,403,311 A * | 4/1995 | Abele et al. | 606/49 |
| 5,419,777 A | 5/1995 | Hofling | |
| 5,489,575 A | 2/1996 | Lee et al. | |
| 5,492,119 A | 2/1996 | Abrams | |
| 5,499,971 A | 3/1996 | Shapland et al. | |
| 5,507,724 A | 4/1996 | Hofmann et al. | |
| 5,536,267 A * | 7/1996 | Edwards et al. | 606/41 |
| 5,569,160 A | 10/1996 | Sauer et al. | |
| 5,569,217 A | 10/1996 | Luther | |
| 5,571,215 A | 11/1996 | Sterman et al. | |
| 5,588,960 A * | 12/1996 | Edwards et al. | 604/20 |
| 5,591,195 A | 1/1997 | Taheri et al. | |
| 5,653,684 A | 8/1997 | Laptewicz et al. | |
| 5,661,133 A | 8/1997 | Leiden et al. | |
| 5,662,124 A | 9/1997 | Wilk | |
| 5,693,029 A | 12/1997 | Leonhardt | |
| 5,698,531 A | 12/1997 | Nabel et al. | |
| 5,702,359 A * | 12/1997 | Hofmann et al. | 604/20 |
| 5,733,280 A | 3/1998 | Avitall | |
| 5,797,870 A | 8/1998 | March et al. | |
| 5,797,960 A | 8/1998 | Stevens et al. | |
| 5,820,592 A | 10/1998 | Hammerslag | |
| 5,827,216 A | 10/1998 | Igo et al. | |
| 5,830,993 A | 11/1998 | Blecha et al. | |
| 5,833,658 A | 11/1998 | Levy et al. | |
| 5,840,031 A | 11/1998 | Crowley | |
| 5,840,059 A | 11/1998 | March et al. | |
| 5,840,062 A | 11/1998 | Gumaste et al. | |
| 5,843,050 A | 12/1998 | Jones et al. | |
| 5,846,220 A * | 12/1998 | Elsberry | 604/500 |
| 5,846,221 A | 12/1998 | Snoke et al. | |
| 5,846,225 A | 12/1998 | Rosengart et al. | |
| 5,857,464 A | 1/1999 | Desai | |
| 5,860,953 A | 1/1999 | Snoke et al. | |
| 5,865,811 A | 2/1999 | Doying, Sr. et al. | |
| 5,871,495 A | 2/1999 | Mueller | |
| 5,876,373 A * | 3/1999 | Giba et al. | 604/95.04 |
| 5,882,332 A | 3/1999 | Wijay | |
| 5,885,272 A | 3/1999 | Aita et al. | |
| 5,891,133 A | 4/1999 | Murphy-Chutorian | |
| 5,931,831 A | 8/1999 | Linder | |
| 5,935,063 A | 8/1999 | Nguyen | |
| 5,941,845 A | 8/1999 | Tu et al. | |
| 5,941,868 A | 8/1999 | Kaplan et al. | |
| 5,944,715 A * | 8/1999 | Goble et al. | 606/41 |
| 5,951,516 A | 9/1999 | Bunyan | |
| 5,964,754 A | 10/1999 | Osypka | |
| 5,971,983 A | 10/1999 | Lesh | |
| 5,993,434 A * | 11/1999 | Dev et al. | 604/501 |
| 5,993,443 A | 11/1999 | Murphy-Chutorian et al. | |
| 5,997,509 A | 12/1999 | Rosengart et al. | |
| 5,997,525 A | 12/1999 | March et al. | |
| 6,004,269 A | 12/1999 | Crowley et al. | |
| 6,004,295 A | 12/1999 | Langer et al. | |
| 6,012,457 A | 1/2000 | Lesh | |
| 6,024,703 A | 2/2000 | Zanelli et al. | |
| 6,055,453 A * | 4/2000 | Hofmann et al. | 604/21 |
| 6,063,022 A | 5/2000 | Ben-Haim | |
| 6,133,233 A | 10/2000 | Ross et al. | |
| 6,161,543 A | 12/2000 | Cox et al. | |
| 6,171,303 B1 | 1/2001 | Ben-Haim et al. | |
| 6,174,307 B1 * | 1/2001 | Daniel et al. | 606/15 |
| 6,179,809 B1 | 1/2001 | Khairkhahan et al. | |
| 6,183,444 B1 | 2/2001 | Glines et al. | |
| 6,224,584 B1 | 5/2001 | March et al. | |
| 6,237,605 B1 | 5/2001 | Vaska et al. | |
| 6,238,389 B1 * | 5/2001 | Paddock et al. | 606/41 |
| 6,241,701 B1 * | 6/2001 | Hofmann | 604/21 |
| 6,254,573 B1 * | 7/2001 | Haim et al. | 604/157 |
| 6,258,086 B1 * | 7/2001 | Ashley et al. | 606/41 |
| 6,264,650 B1 * | 7/2001 | Hovda et al. | 606/32 |
| 6,309,375 B1 | 10/2001 | Glines et al. | |
| 6,314,962 B1 | 11/2001 | Vaska et al. | |
| 6,314,963 B1 | 11/2001 | Vaska et al. | |
| 6,416,490 B1 * | 7/2002 | Ellis et al. | 604/22 |
| 6,554,794 B1 * | 4/2003 | Mueller et al. | 604/95.04 |
| 6,575,931 B1 * | 6/2003 | Ponzi | 604/95.01 |
| 6,689,103 B1 | 2/2004 | Palasis | |
| 6,902,562 B1 * | 6/2005 | Negus et al. | 606/7 |
| 2001/0034501 A1 | 10/2001 | Tom | |

FOREIGN PATENT DOCUMENTS

| | | |
|---|---|---|
| WO | WO 97/25101 | 7/1997 |
| WO | WO 97/47253 | 12/1997 |
| WO | WO 98/05307 | 2/1998 |
| WO | WO 99/39624 | 8/1999 |
| WO | WO 99/44656 | 9/1999 |
| WO | WO 99/49926 | 10/1999 |
| WO | WO 00/18462 | 4/2000 |
| WO | WO 00/56224 | 9/2000 |
| WO | WO 00/57895 | 10/2000 |

OTHER PUBLICATIONS

Padua et al., "Basic fibroblast growth factor is cardioprotective in ischemia-reperfusion injury" Molecular and Cellular Biochemistry 143: 129-135 (1995).

Shi et al., "PR-39, a proline-rich antibacterial peptide that inhibits phagocyte NADPH oxidase activity by binding to Src homology 3 domains of p47phox" Proc. Natl. Acad. Sci. 93:6014-6018 (1996).

Uchida et al., "Angiogenic therapy of acute myocardial infarction by intrapericardial injection of basic fibroblast growth factor and heparin sulfate: An experimental study" Am. Heart J., 130:1182-1188 (1995).

Unger et al. "Basic fibroblast growth factor enhances mycardial collateral flow in a canine model" Am J. Physiol., 266:H1577-H1595 (1994).

Walterberger et al., "Ischemia-Induced Transplant Arteriosclerosis in the Rat" Arteriosclerosis, Thrombosis and Vascular Biology 16(12):1516-1523 (1996).

Xiaobin, et al. "Ischemia and Reperfusion reduce the Endogenous Basic Fibroblast Growth Factor (bf GF) in Rat Skeletal Muscles" Chinese Medical Journal 108(9): 699-703, (1995).

U.S. Appl. No. 60/191,610, filed Mar. 23, 2000, Tom.

Chu V et al., Angiogenic Response Induced by Mechanical Transmyocardial Revascularization, J. Thorac Cardiovasc Surg Nov.; 118(5):849-56 (1999).

Deckelbaum. L.I., Cardiovascular Applications of Laser Technology, Lasers in Surgery and Medicine 15:315-341 (1994).

Frazier, O.H., Myocardial Revascularization with Laser—Preliminary Findings, Circulation, 1995; 92 [suppl II;II-58-II-65].

Kipshidze et al., Therapeutic Angiogenesis in Patients with Advanced Coronary Artery Disease: Hype or Hope?, J Invas Cardiol II (10):589-599 (1999).

Hughes GC et al., Neovascularization After Transmyocardial Laser Recascularization in a Model of Chronic Ischemia, Ann Thorac Surg Dec.;66(6):2029-36 (1998).

Prentice H et al., Ischemic/Reperfused Myocardium Can Expresss Recombinant Protein Following Direct DNA or Retroviral Injection, J Mol Cell Cardiol Jan.;28(1): 133-40 (1996).

Sayeed-Shah U et al., Complete Reversal of Ischemic Wall Motion Abnormalities by Combined Use of Gene Therapy with Transmyocardial Lasaer Revascularization, J Thorac Cardiovasc Surg Nov.;116(5):763-9 (1998).

Spanier T et al., Angiogenesis: A Possible Mechanism Underlying the Clinical Benefits of Transmyocardial Laser Revascularization, J Clin Laser Med Surg Dec.;15(6):269-73 (1997).

Yamamoto N et al., Angiogenesis is Enhanced in Ischemic Canine Myocardium by Transmyocardial Laser Revascularization, J Am Coll Cardiol May;31(6):1426-33 (1998).

* cited by examiner

METHOD AND APPARATUS FOR TREATING ISCHEMIC TISSUE

RELATED APPLICATION

This application claims priority to U.S. Provisional Patent Application Ser. No. 60/214,053 filed on Jun. 26, 2000 which is incorporated in its entirety herein by reference.

FIELD OF THE INVENTION

The present invention relates to methods and devices for treating a patient at risk of loss of cardiac function by cardiac ischemia.

BACKGROUND OF THE INVENTION

Heart disorders are a common cause of death in developed countries. They also impair the quality of life of millions of people and restrict activity by causing pain, breathlessness, fatigue, fainting spells and anxiety. The major cause of heart disease in developed countries is impaired or inadequate blood supply to the heart. The coronary arteries may become narrowed due to arteriosclerosis and part of the heart muscle is deprived of oxygen and other nutrients. The resulting ischemia or blockage can lead to angina pectoris, a pain in the chest, arms or jaw due to lack of oxygen to the heart's myocardium, infarction or tissue necrosis in myocardial tissue. Alternatively, and particularly with age, the extent of vascularization of the heart may diminish, leaving the heart undersupplied with oxygen even in the absence of significant arteriosclerosis.

Coronary-artery blockage can be relieved in a number of ways. Therapeutic-substance therapy, including nitrates, beta-blockers, and peripheral vasodilator drugs (to dilate the arteries) or thrombolytic drugs (to dissolve clots) can be very effective. If therapeutic-substance treatment fails, transluminal angioplasty is often indicated—the narrowed part of the artery, clogged with atherosclerotic plaque or other deposits, can be stretched apart by passing a balloon to the site and gently inflating it a certain degree. In the event therapeutic-substance therapy is ineffective or angioplasty is too risky (introduction of a balloon in an occluded artery can cause portions of the arteriosclerotic material to become dislodged which may cause a total blockage at a point downstream of the subject occlusion, thereby requiring emergency procedures), the procedure known as coronary artery bypass grafting (CABG) is the most common and successful major heart operation performed, with over 500,000 procedures done annually in America alone. A length of vein is removed from another part of the body. The section of vein is first sewn to the aorta and then sewn onto a coronary artery at a place such that oxygenated blood can flow directly into the heart. CABG typically is performed in an open chest surgical procedure, although recent advances suggest minimally invasive surgery (MIS) techniques may also be used.

Another method of improving myocardial blood supply is called transmyocardial revascularization (TMR), the creation of channels from the epicardial to the endocardial portions of the heart. Initially, the procedure used needles to perform "myocardial acupuncture," and has been experimented with at least as early as the 1930s and used clinically since the 1960s, see Deckelbaum, L. I., Cardiovascular Applications of Laser Technology, *Lasers in Surgery and Medicine* 15:315-341 (1994). This procedure has been likened to transforming the human heart into one resembling that of a reptile. In the reptile heart, perfusion occurs via communicating channels between the left ventricle and the coronary arteries. Frazier, O. H., Myocardial Revascularization with Laser—Preliminary Findings, *Circulation,* 1995; 92 [suppl II:II-58-11-65]. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. The needle technique was not continued because the channels did not remain open, replaced by the use of laser energy to accomplish TMR.

Therapeutic-substance therapies with angiogenic growth factors may expedite and/or augment collateral artery development. Therapeutic-substance therapies, when combined with other treatments such as TMR or other injury causing methods may substantially increase the effectiveness of treatment over either treatment individually. To accomplish these needs, therapeutic-substance transfer devices for delivering precise amounts of these therapeutic-substances can enhance this healing process when coupled with an initial injury process. Surgeons who deal with minimally invasive surgical techniques, and interventional cardiologists who deal with percutaneous approaches, need devices for therapeutic-substance delivery procedures that also provide a localized injury with minimal effort or the need to introduce multiple tools or devices into the patient's body. Moreover, the therapeutic-substances used in modern medical technology are often quite expensive, potentially mixing and/or handling sensitive, and it is a new challenge to make these therapeutic-substances or other compounds readily available for precise, predetermined delivery during these advanced or other procedures while combined with other mechanical treatments such as TMR or other injury type treatments. Therefore, a unified device which provides the advantages of precise and localized therapeutic-substance delivery coupled with localized injury infliction in a region predetermined by the device with respect to therapeutic-substance delivery would be highly desired over existing methods of using two or more distinct tools or devices that do not provide for a precise and predetermined spatial relation between the sites for therapeutic-substance delivery and the site or sites for injury. The invention provided herein addresses these needs and provides these desired advantages in an efficient, minimally invasive, and cost effective manner.

SUMMARY OF THE INVENTION

The invention provides methods and devices for stimulating angiogenesis in or near ischemic heart tissue, and for stimulating regeneration of tissue. In preferred embodiments, the device comprises an elongate shaft having proximal and distal ends, a lumen extending therebetween, and a control structure for actuation of the device by user operation. Such device further has at least one injury effector adjacent the elongate shaft's distal end, and capable of inducing a site of injury in response to actuation by the control structure, and at least one therapeutic-substance delivery effector carried on the elongate shaft at the distal end thereof. The therapeutic-substance delivery effector has at least one therapeutic-substance delivery port through which therapeutic-substance can be delivered from the effector into tissue against which the effector is placed in response to operation of the control structure. Each of the injury-treatment effectors and the therapeutic-substance delivery effectors are spaced from one another at selected positions and adapted to be placed simultaneously against tissues to be treated. The device has at least one therapeutic-substance source that includes a reservoir for storing a substance which is in substance communication with the therapeutic-substance delivery ports, and responsive to the control structure to eject therapeutic-substance solution from the reservoir through the ports into such tissue. The device is constructed such that the control structure, when activated by a user operating to actuate said injury-treatment effector, actuates said therapeutic-substance delivery effector and actuates said therapeutic-substance source. Consequently, therapeutic-substance solution is expelled through the therapeutic-substance delivery ports resulting in one or more sites of injury adjacent one or more sites of therapeutic-substance infusion in the tissue at pre-selected locations.

In other embodiments, the invention further provides for a third treatment effector for creating a treatment position marker. Other embodiments provide for a third treatment effector that is separate from the injury and therapeutic-substance delivery effectors. Yet other embodiments provide for a marking effector in combination with either the injury, or therapeutic-substance delivery, or injury and therapeutic-substance delivery effectors.

The invention further provides in other embodiments, a device where the injury and therapeutic-substance delivery effectors actuate simultaneously. In still other embodiments, the injury and the therapeutic-substance delivery effectors actuate sequentially. And in still others, the injury, therapeutic-substance delivery, and position-marking effectors actuate simultaneously. Yet others provide for the injury, therapeutic-substance delivery, and position-marking effectors to actuate sequentially, and in others, the position-marking effector actuates independently from the injury effectors or therapeutic-substance delivery effectors. Furthermore, other embodiments provide for the therapeutic-substance-source to actuate independent of the actuation of the therapeutic-substance delivery effectors, and others provide for the therapeutic-substance-source to actuate simultaneously with the actuation of the therapeutic-substance delivery effectors.

Preferred embodiments of the invention provide for the elongate shaft to further comprise a steerable distal end. Other embodiments include an optical viewing port located at the elongate shaft's distal end in optical communication with an imaging device such as a viewfinder lens or a video-imaging device.

The invention further provides for positioning guidance by including in the elongate shaft a contact sensor located on the elongate shaft's distal end. Contact sensors include, for example, force contact transducers and ultrasonic transducers. Some embodiments also include a positioning aid located on the elongate shaft's distal end, such as a suction cup in substance communication with a user controllable vacuum source to secure the elongate shaft's distal end against a target tissue during administration of each treatment. Other positioning aids include, for example, a hook, a corkscrew anchor, and a frictional surface to prevent skidding.

In yet other embodiments, catheter type embodiments of the invention are able to maintain the distal end's position adjacent a target tissue during use by further including an anchor catheter. The anchor catheter is slidably situated within a third catheter having at least two lumens. The first lumen is occupied by a first catheter having an injury, treatment, and optionally marking effectors as described above, and a second lumen occupied by a second catheter having a distal end having an anchor adjacent to the second catheter distal end adapted to anchoring to an adjacent target tissue. Either the first or second catheter, or both, is capable of moving away from the other as the third catheter is withdrawn relative to both the first and second catheters, thus longitudinally exposing the first and second catheter, where then the first catheter and second catheter distal ends move away from each other a selectable distance, selected by how much a user withdraws the third catheter, and further wherein the injury and treatment effector catheter is adapted to move circumferentially about the first anchor catheter upon axial rotation of the third catheter while maintaining functional contact with the target tissue surface. In use, the third catheter is withdrawn partly as it is rotated axially. This process is continued until a spiral pattern covering the entire target area is treated.

In preferred embodiments, the elongate shaft is in the form of a catheter. In yet other preferred embodiments, the elongate shaft is an endoscope further comprising a viewing conduit optically connecting the distal end of the device to a remote viewer and optionally including an illuminator located on the distal end of the device, and both to aid a user in navigating the distal end of the device. In particularly preferred embodiments, the elongate shaft is an open surgical hand held device optionally in optical communication with a remote view and optionally in optical communication with an illumination source.

The invention further provides for a device for treating ischemic tissue comprising an elongate shaft having proximal and distal ends, a lumen extending therebetween, a control structure operably connected to the shaft for actuation of the device by user activation, at least one injury effector adjacent the elongate shaft's distal end, and capable of inducing a mechanical or energy injury produced at a tissue site in response to actuation by the control structure when the shaft's distal end is placed against a tissue surface, at least one therapeutic-substance delivery effector carried on the elongate shaft at the distal end thereof, said therapeutic-substance delivery effector having at least one therapeutic-substance delivery port through which therapeutic-substance can be delivered from the effector into tissue against which the effector is placed, each of said one or more injury-treatment effectors and said one or more therapeutic-substance delivery ports being spaced from one another at selected positions and adapted to be placed simultaneously against such tissues, and at least one therapeutic-substance source having a reservoir for storing a substance and in substance communication with said therapeutic-substance delivery ports, and responsive to said control structure to eject therapeutic-substance from said reservoir through said one or more ports into such tissue, wherein, said control structure, when activated by a user, operates to actuate said injury-treatment effector, and additionally actuates said therapeutic-substance source to expel therapeutic-substance through said one or more ports to create one or more sites of therapeutic-substance infusion in the tissue at defined spaced-apart locations with respect to the created one or more sites of injury.

The invention further provides for method of treating ischemic tissue. Preferred methods include methods comprising the steps of:
  identifying target tissue regions of ischemic tissue,
  providing a device that can, upon activation and by a single placement of the device, cause an injury to at least one site of target tissue different than at least one site of target tissue where a therapeutic-substance is delivered,
  placing the device against the identified target tissue, and
  activating the device to cause injury to selected sites within the target tissue, and to cause therapeutic-substance to be delivered to regions in the target tissue at preselected sites away from the sites of injury.

Another embodiment of the invention provides a method for treating a target tissue comprising the steps of:
  identifying the target tissue, producing one or more sites of injury within said region, where multiple sites of injury, if produced, are at known relative positions with respect to one another, and infusing therapeutic-substance into one or more sites different than the one or more sites of injury.

Another embodiment provides a method for treating ischemic tissue comprising the steps of:

identifying a region of ischemic tissue within a patient's body, producing one or more sites of injury within such region, where multiple sites, if produced, are at known relative positions with respect to one another, and infusing therapeutic-substance into one or more sites different from such injury sites and at known positions away from such injury sites.

BRIEF DESCRIPTION OF THE DRAWINGS

FIGS. 11a-1 through 11d-2 depicts effector arrangements and corresponding results.

FIGS. 12a-1 through 12d-2 depicts effector arrangements and corresponding results.

DETAILED DESCRIPTION OF THE DRAWINGS

Figure 1:
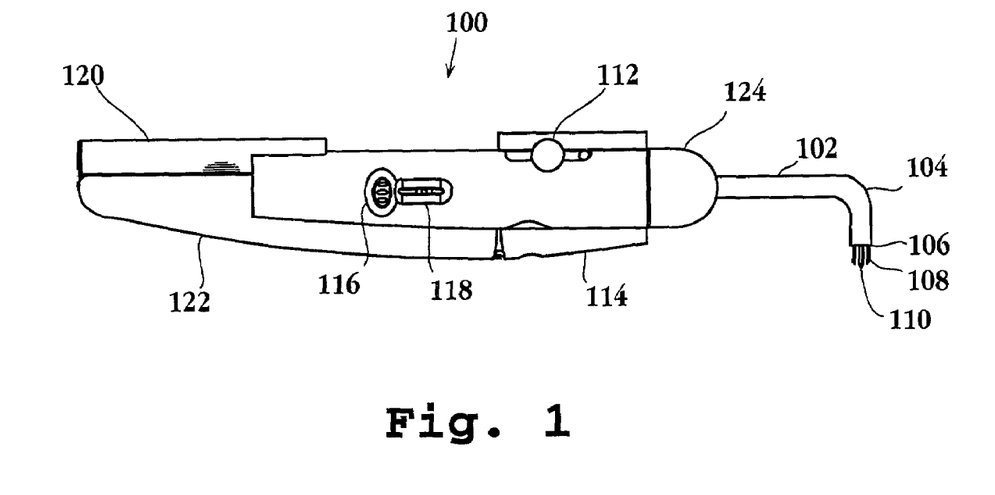
FIG. 1 depicts a hand held open surgery embodiment of the invention.

FIG. 1 depicts a hand held open surgery embodiment of the invention. Device 100 has elongate shaft 102 with bend 104 terminating at elongate shaft's 102 distal end 106 having therapeutic-substance delivery effectors 108 flanking injury effector 110. Proximal end 122 has a therapeutic-substance reservoir, not shown, located under access door 120. Therapeutic-substance delivery control 116 is located next to therapeutic-substance-volume indicator 118 and work together to administer therapeutic-substance and track the position and volume of the therapeutic-substance reservoir. Thumbwheel 112 actuates a pull-wire, not shown, situated inside of elongate shaft 102, and causes bend 104 to form from otherwise straight but selectably flexible elongate shaft 102 when actuated. Trigger 114, when operated by a user, actuates both therapeutic-substance delivery effectors 108 and injury effectors 110 thrusting forward, away from the elongate shaft's distal end, and into a tissue which the device is placed against. Further operation of the trigger causes actuation of the injury effector to cause injury to a target tissue site, not shown. Yet further operation of the trigger causes actuation of the therapeutic-substance reservoir thereby resulting in the expulsion of therapeutic-substance from the therapeutic-substance delivery ports, not shown, situated on the distal end of therapeutic-substance delivery effectors 108. Neck 124 is rotatable about the longitudinal axis of elongate shaft 102 to permit rotation of elongate shaft 102 with respect to proximal end 122. Optional injury energy supply cable, not shown, is connected to proximal end 122 to supply injury energy, such as RF electrical signal, to injury effectors 110 in communication with the an injury energy supply. Other embodiments use a fiber optic to optically connect a light mediated ablation injury effector with an injury supply energy such as a laser.

Figure 2:
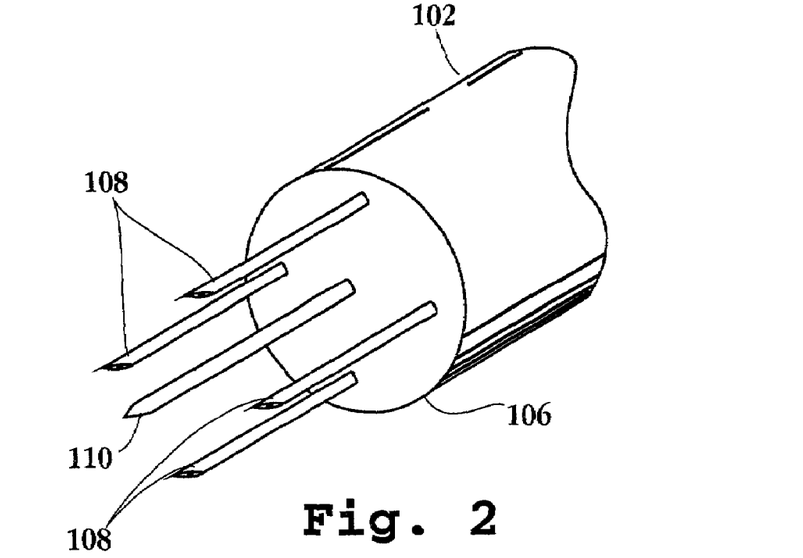
FIG. 2 depicts a close-up view of elongate shaft's 102 distal end 106.

FIG. 2 depicts a close-up view of elongate shaft's 102 distal end 106. Here, injury effector 110 is surrounded by therapeutic-substance delivery effectors 108, the injury effector 110 and therapeutic-substance delivery effectors 108 being shown in their extended position protruding out from the distal end 106.

Figure 3:
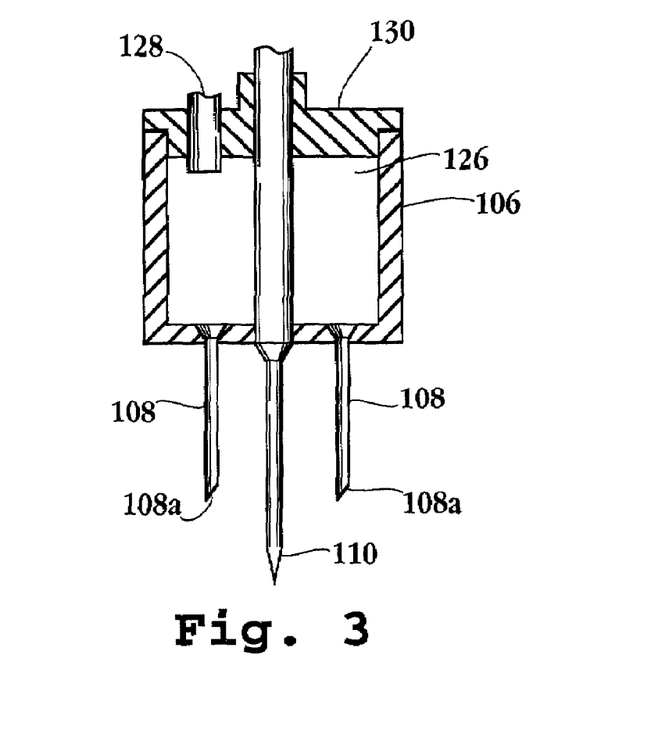
FIG. 3 depicts a cross-sectional view of distal end 106 having radially distributed therapeutic-substance delivery effectors 108 distributed about centrally located injury effector 110.

FIG. 3 depicts a cross-sectional view of distal end 106 having radially distributed therapeutic-substance delivery effectors 108 distributed about centrally located injury effector 110. Cap 130 closes off lumen 126 created by distal end 106. Injury effector 110 passes through lumen 126 and is electrically isolated from lumen 126 where electrical energy is used as an injury energy. Distal end input port 128 is in substance communication with lumen 126 and adjacent therapeutic-substance delivery effectors 108 and therapeutic-substance delivery ports 108a and is in substance communication with a therapeutic-substance reservoir, not shown.

Figure 4:
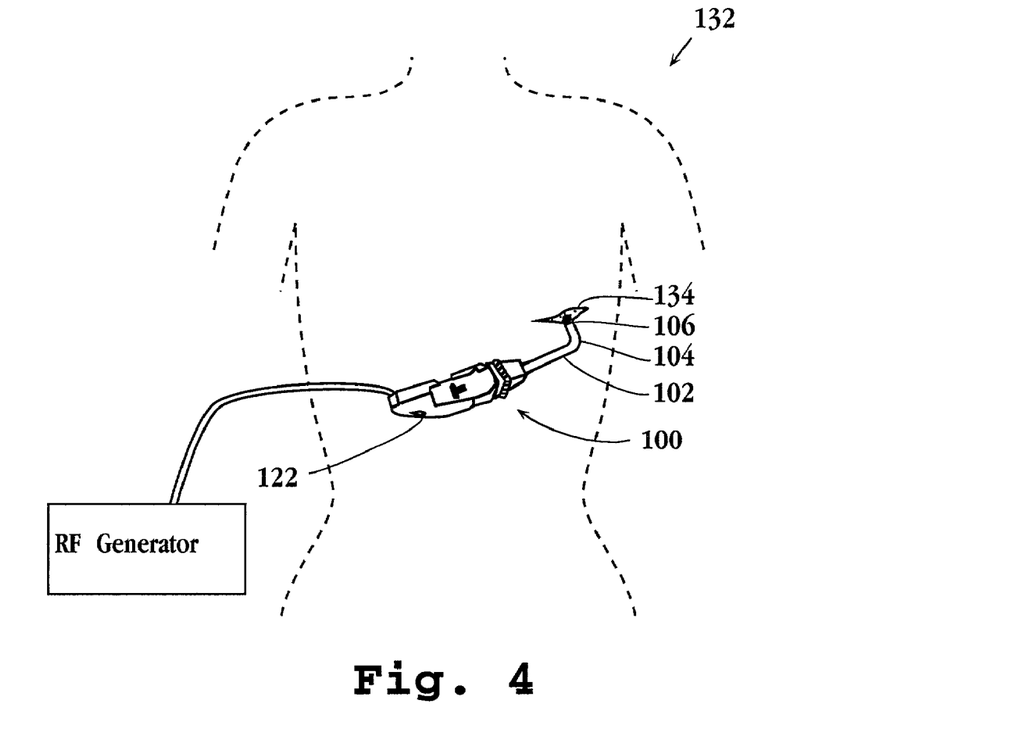
FIG. 4 depicts a hand held open surgery embodiment of the invention inserted slightly into a patient.

FIG. 4 depicts a hand held open surgery embodiment of the invention inserted slightly into a patient. Patient 132 has previously made thoracotomy 134 where distal end 106 of elongate shaft 102 of device 100 is placed inside patient 132 to access a remote tissue. Device 100 may be axially swiveled to provide optimal contact between the target tissue, not shown, and distal end 106.

Figure 5A:
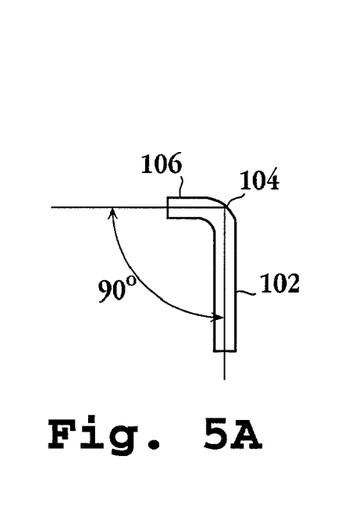
FIGS. 5a-5c depict various angles of bend 104 of elongate shaft 102.
Figure 5B:
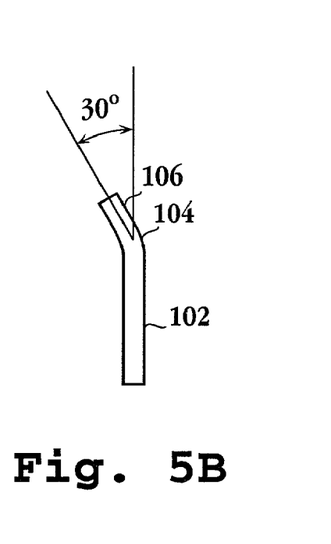
Figure 5C:
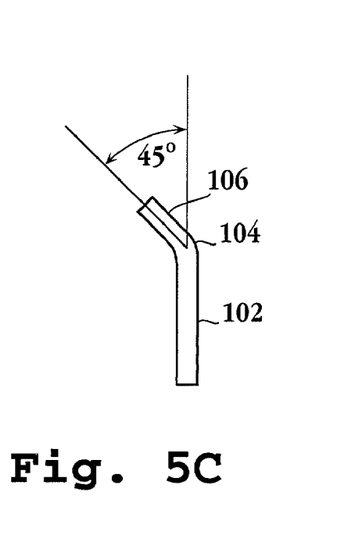

FIGS. 5a-5c depict various angles of bend 104 of elongate shaft 102. Such angles may be achieved by either setting a fixed bend angle at the time of manufacture of the device, or by making elongate shaft's 102 distal end 106 directly bendable by designing it so that a user may grasp distal end 102 and proximal end 122, and introduce bend 104 by bending. Straightness can be attained by re-bending elongate shaft 102 to a straight configuration. Other embodiments provide for a steering mechanism using pull wires, not shown, to steer an angle into the distal end 106 by inducing bend 104.

Figure 6A:
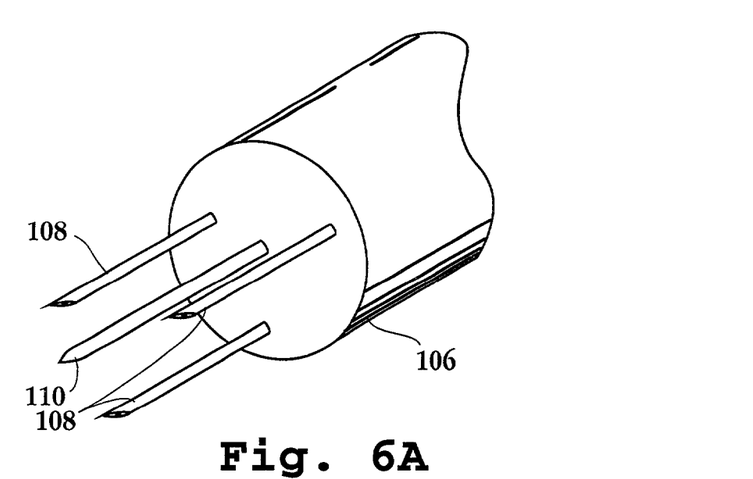
FIGS. 6a-6e depict several examples of various configurations of effectors provided by the invention.
Figure 6B:
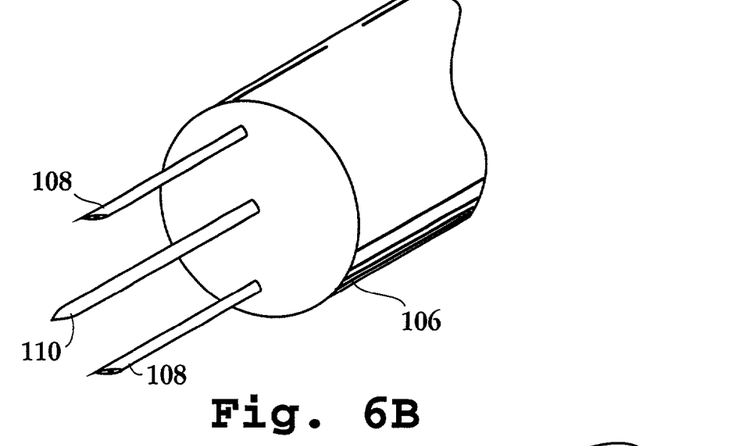
Figure 6C:
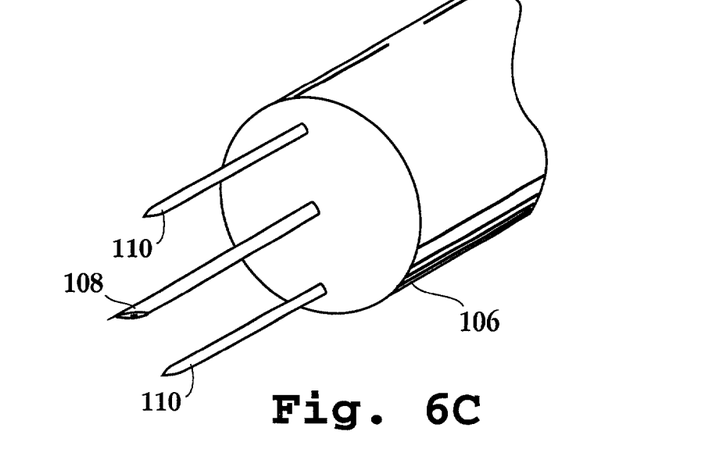
Figure 6D:
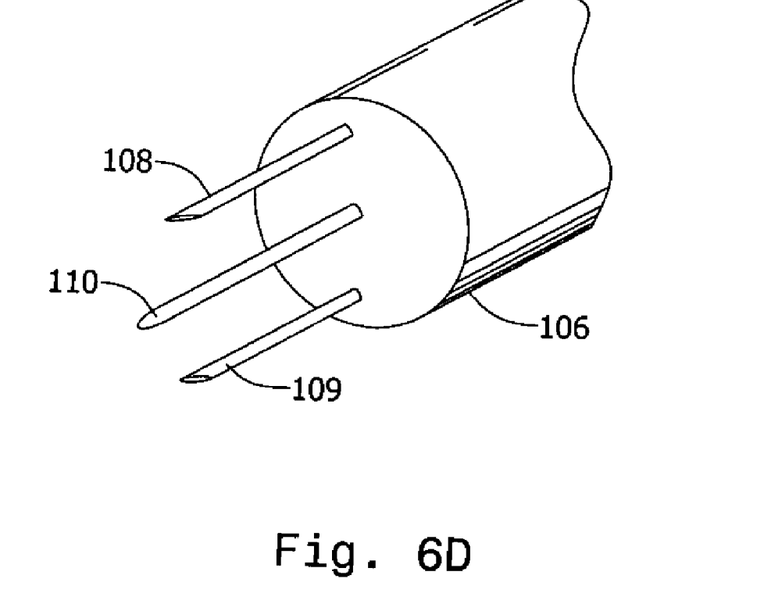
Figure 6E:
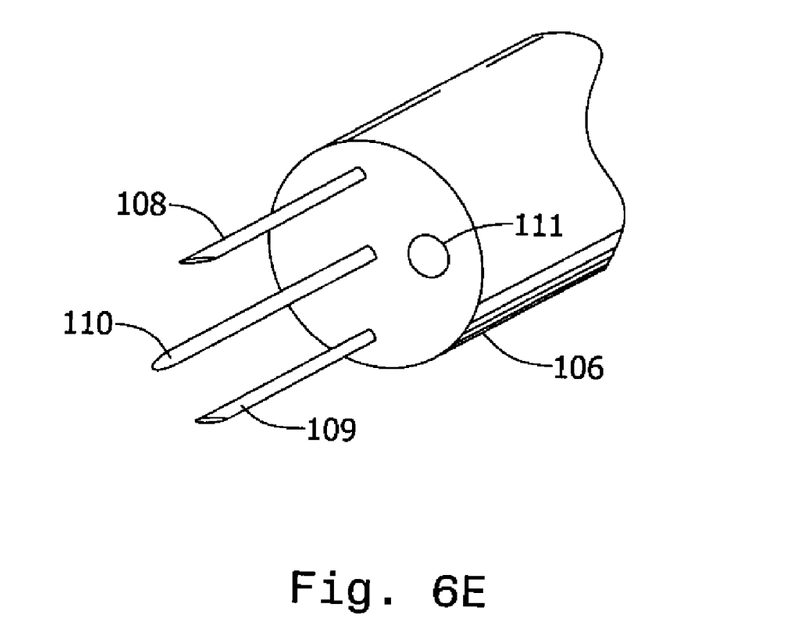

FIGS. 6a-6e depict several examples of various configurations of effectors provided by the invention. FIG. 6a depicts distal end 106 with three therapeutic-substance delivery effectors 108 in their extended position surrounding a single injury effector 110 in an extended position. FIG. 6b depicts distal end 106 with two therapeutic-substance delivery effectors 108 in their extended position flanking a single injury effector 110 in an extended position. FIG. 6c depicts distal end 106 with two injury effectors 110 in their extended position flanking a single therapeutic-substance delivery effector 108 in an extended position. FIG. 6d depicts distal end 106 with a single therapeutic-substance delivery effector 108 in an extended position, a single injury effector 110 in an extended position, and a single marking effector 109 in an extended position. FIG. 6e depicts distal end 106 of FIG. 6d further including endoscope 111.

Figure 7:
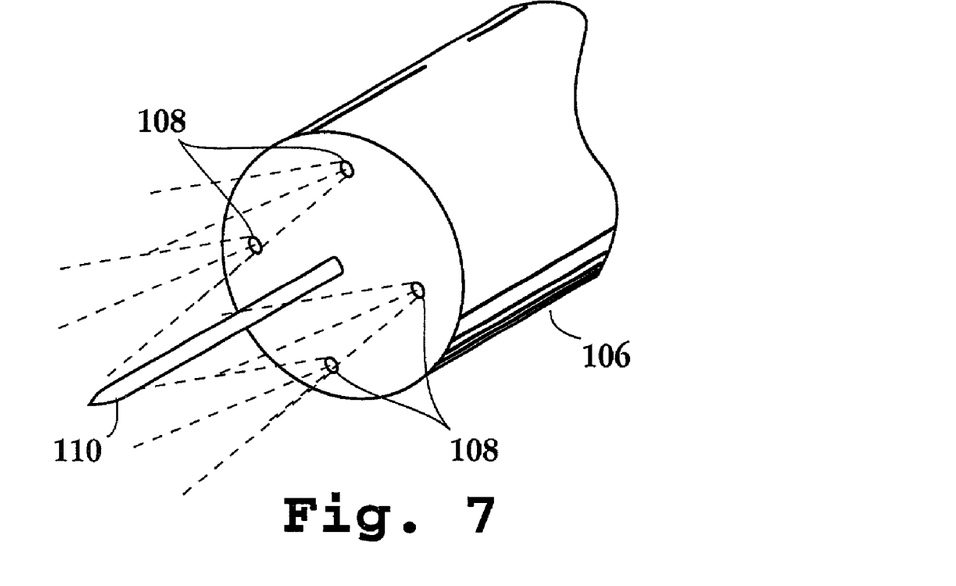
FIG. 7 depicts a preferred embodiment of distal end 106 where therapeutic-substance delivery effectors 108 are hydraulic jets and injury effector 110 is an RF electrical probe.

FIG. 7 depicts a preferred embodiment of distal end 106 where therapeutic-substance delivery effectors 108 are hydraulic jets and injury effector 110 is an RF electrical probe.

Figure 8:
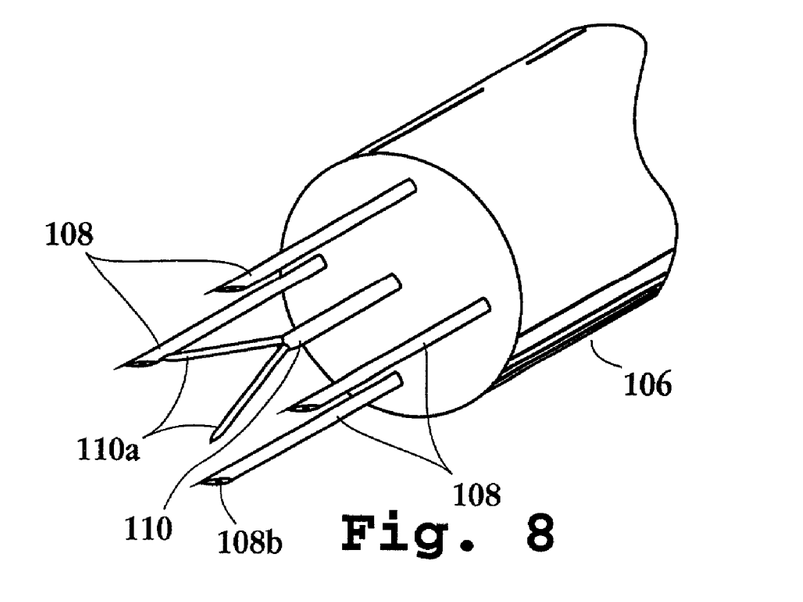
FIG. 8 depicts a preferred embodiment.

FIG. 8 depicts a preferred embodiment of distal end 106 where therapeutic-substance delivery effectors 108 are syringe needles having ports 108b and injury effector 110 is a conical cutting tool comprising a protruding off-axis element 110a that is inserted into the target tissue, not shown, and causes a conical cut upon axial rotation.

Figure 9:
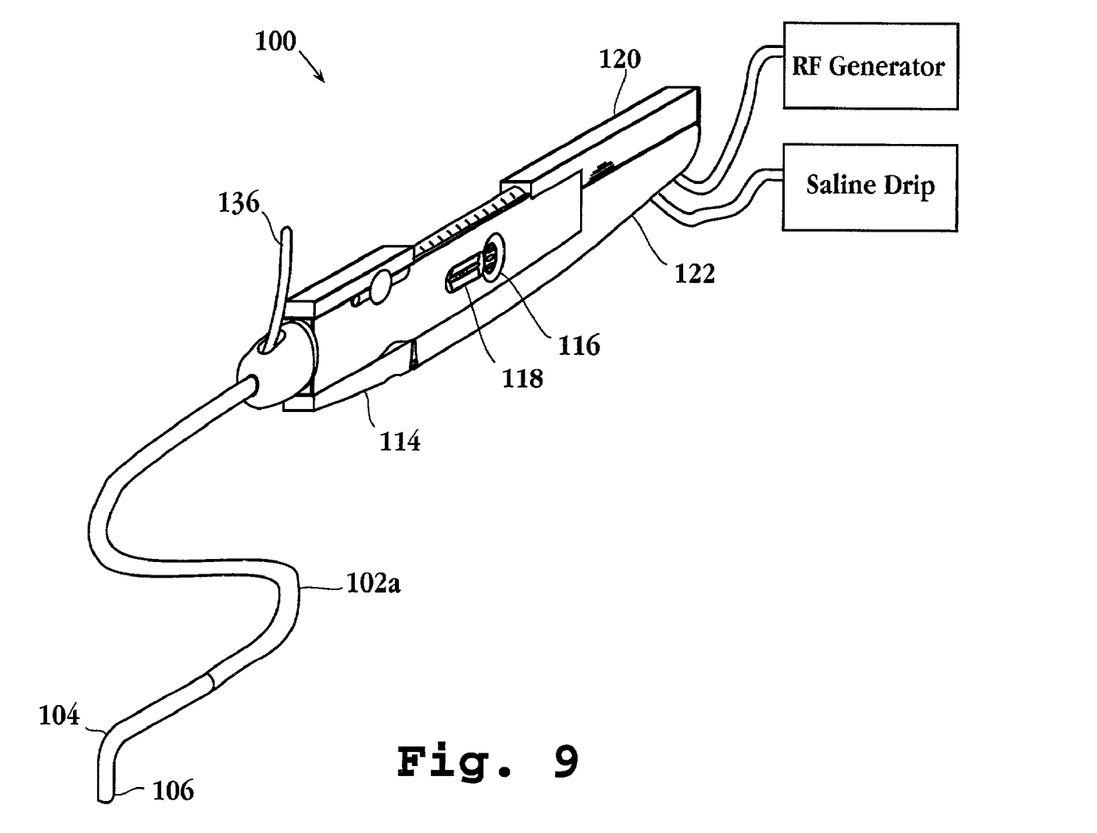
FIG. 9 depicts a view of a catheter based, minimally invasive embodiment of the invention.

FIG. 9 depicts a view of a catheter based, minimally invasive embodiment of the invention. Here, elongate shaft 102, not shown, is housed coaxially inside catheter 102a. Distal end 106 is shown with bend 104 resulting from actuation of a steering mechanism through control 136. In other embodiments, control 136 actuates independently the injury effectors and another, not shown, control actuates the catheter steering mechanism.

Figure 10A:
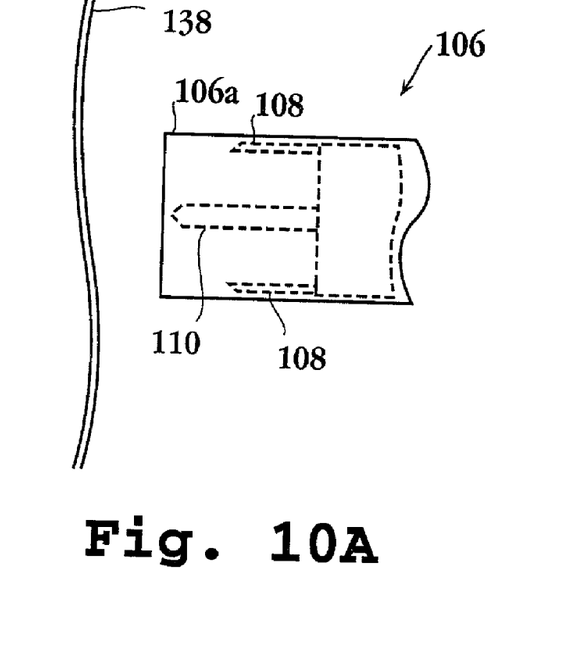
FIGS. 10a and 10b depict different states of one embodiment of the invention in use.
Figure 10B:
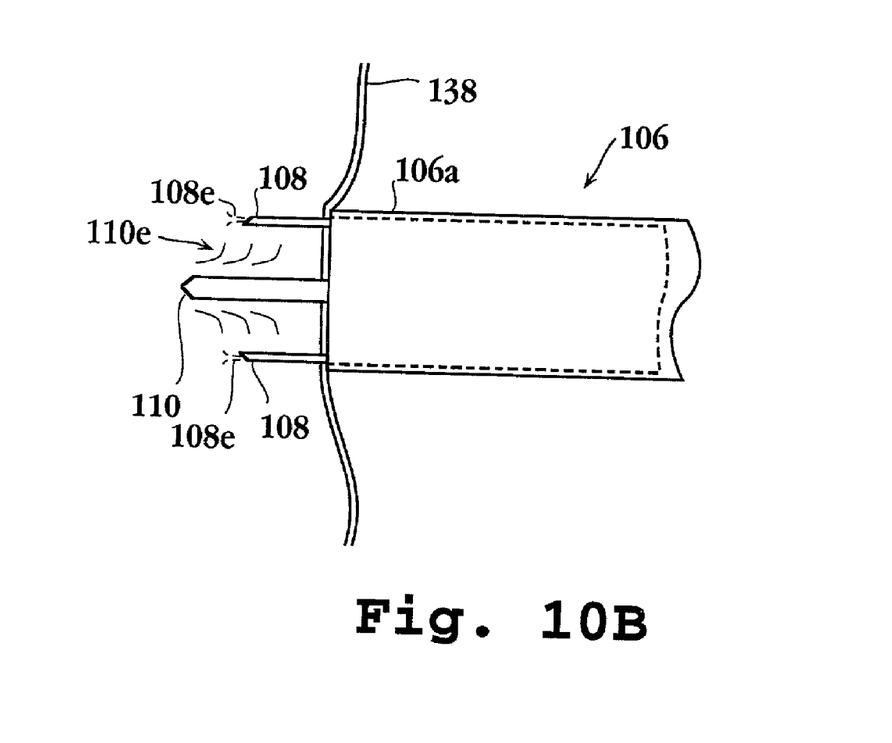

FIGS. 10a and 10b depict different states of one embodiment of the invention in use. Distal end 106 further includes sheath 106a that normally covers extended therapeutic-substance delivery effectors 108 and injury effector 110. FIG. 10a depicts the state of distal end 106 just before contacting target tissue 138 with sheath 106a extended. FIG. 10b depicts distal end 106 after contacting target tissue 138 where sheath 106a retracts upon contact. Therapeutic-substance delivery effectors 108 have penetrated target tissue 138 and have expelled therapeutic-substance into therapeutic-substance-cavity 108e formed by the penetration of therapeutic-substance delivery effectors 108. Injury effector 110 has also penetrated target tissue 138 and created injury 110e. Upon withdrawal of distal end 106 away from target tissue 138, distal end 106 returns to the position depicted in FIG. 10a. In some preferred embodiments, it is therapeutic-substance delivery effectors 108 and injury effectors 110 that extend towards target tissue 138 from sheath 106a which is in a fixed relation to device 100's proximal end 122. Sheath 196a, in particularly preferred embodiments, forms a tip cap (not shown) having a tip distal end with a plurality of apertures that the effectors may protrude through upon actuation. In these embodiments, the tip cap distal end contacts a target tissue, and at selected conditions, the effectors are actuated to move forward into the target tissue through the tip cap distal end apertures where then therapeutic-substances are deposited and injury is made, after which, the effectors are retracted from the target tissue and back into the device through tip cap distal end apertures.

Figure 11A:
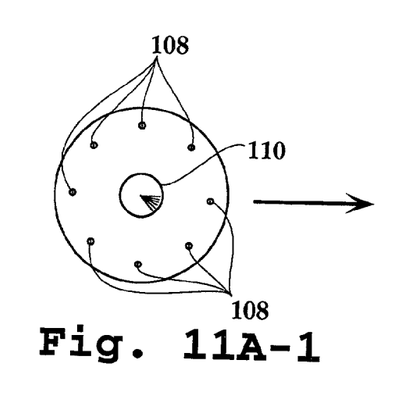
Figure 11A:
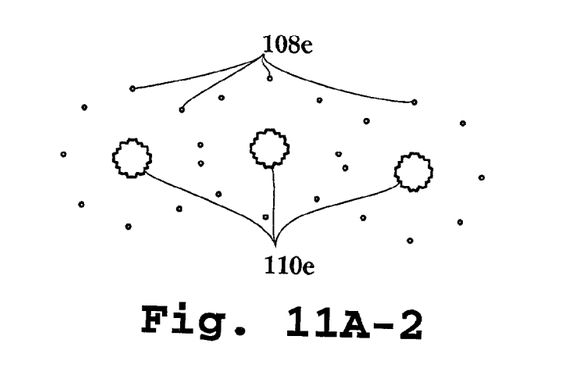
Figure 11B:
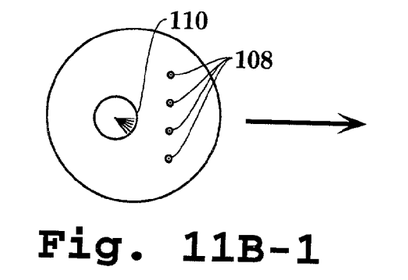
Figure 11B:
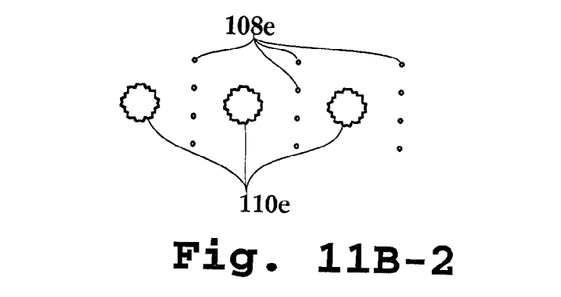
Figure 11C:
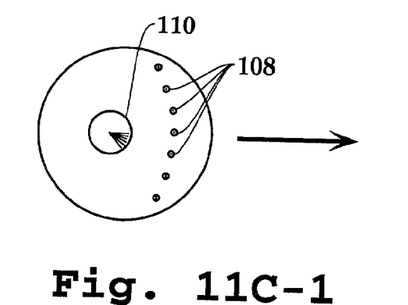
Figure 11C:
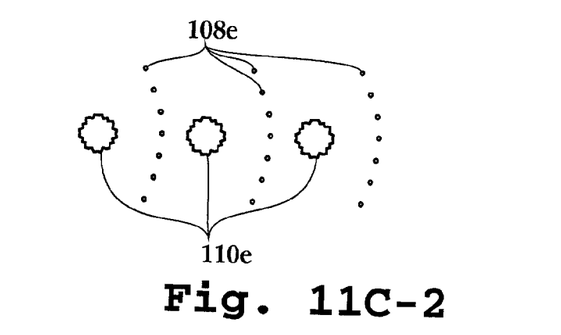
Figure 11D:
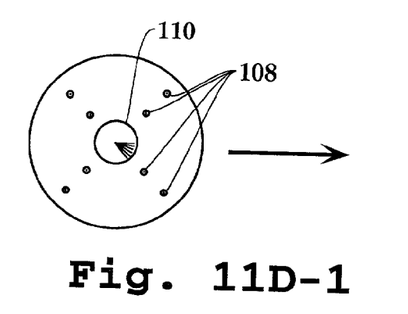
Figure 11D:
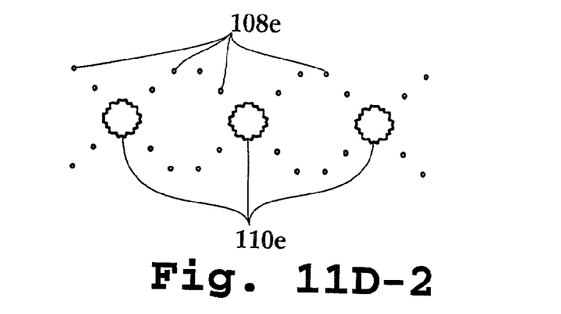

FIGS. 11a-1 through 11d-2 depict effector arrangements and corresponding results. FIGS. 11a-1 through 11d-1 depict cross-sectional arrangements of single injury effectors located among a plurality of therapeutic-substance delivery effectors. FIGS. 11a-2 through 11d-2 depict the resulting pattern of treatments in target tissue from corresponding arrangements applied in a linear fashion. FIG. 11 further depicts the result produced by methods provided by the present invention. The invention provides a method for treating a target tissue comprising the steps of first identifying the target tissue, then producing one or more sites of injury within said region, where multiple sites of injury, if produced, are at known relative positions with respect to one another, and infusing therapeutic-substance into one or more sites different than the one or more sites of injury. Another embodiment provides a method for treating ischemic tissue comprising the steps of first identifying a region of ischemic tissue within a patient's body, and then producing one or more sites of injury within such region, where multiple sites, if produced, are at known relative positions with respect to one another, and infusing therapeutic-substance into one or more sites different from such injury sites and at known positions away from such injury sites.

Figure 12A:
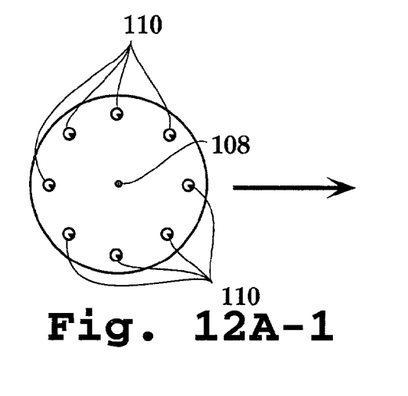
Figure 12A:
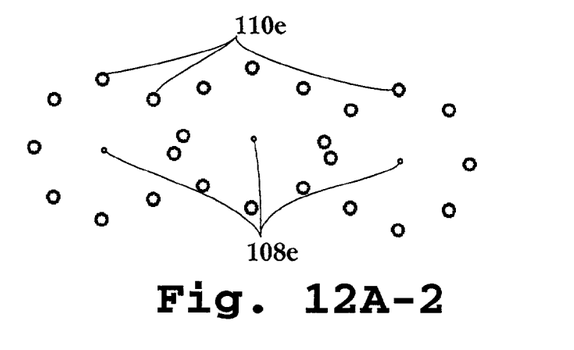
Figure 12B:
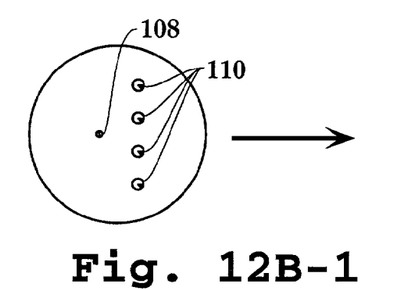
Figure 12B:
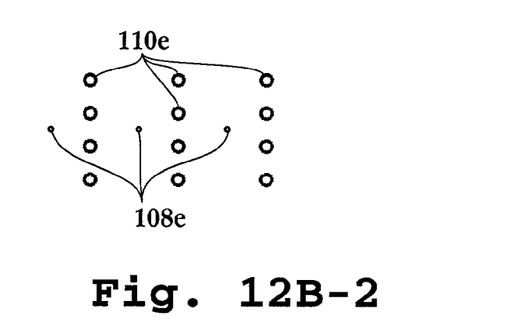
Figure 12C:
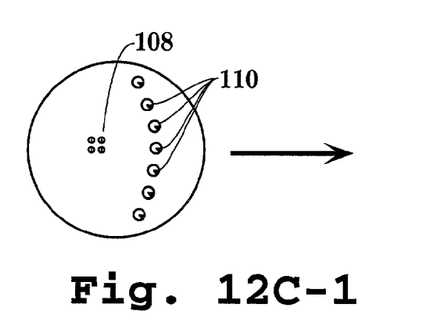
Figure 12C:
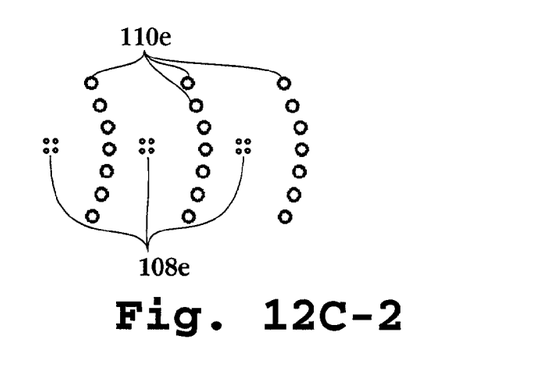
Figure 12D:
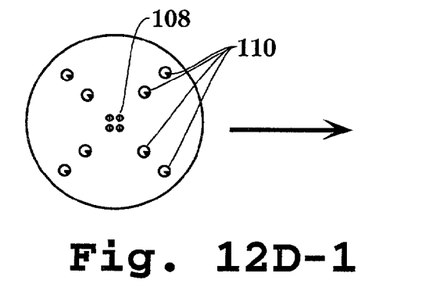
Figure 12D:
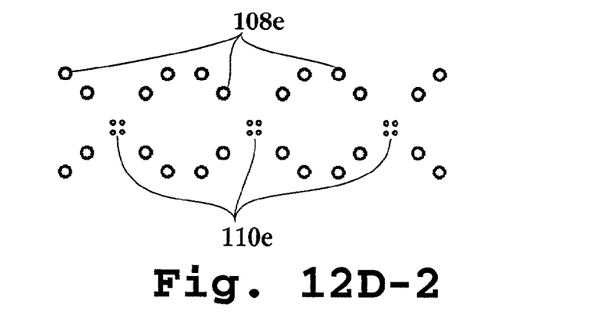

FIGS. 12a-1 through 12d-2 depicts effector arrangements and corresponding results. FIGS. 12a-1 through 12d-1 depict cross-sectional arrangements of multiple injury effectors located among a singular of therapeutic-substance delivery effector. FIGS. 12a-2 through 12d-2 depict the resulting pattern of treatments in target tissue from corresponding arrangements applied in a linear fashion.

The present invention provides methods and devices for stimulating angiogenesis in or near ischemic heart tissue, and for stimulating regeneration of tissue. The invention provides a combination of two, or optionally three, different treatments with the single placement of one device against a tissue targeted for enhanced vascularization. Treatments are applied through separate treatment effectors. The first treatment creates a site of injury. The second treatment infuses a substance, for example, therapeutic-substance compounds or cells, into a position selected away from the injury site at pre-selected and fixed locations away from the first injury site. The third, optional, treatment creates a position marker site so that a user may later identify tissue regions previously treated by the device of the present invention. Each treatment may occur in sequential order in any combination, or simultaneously, or may occur as a combination of sequential and simultaneous events. After all of the events occur, the treated area then has one or more sites of injury caused by the first treatment. The injury site or sites are surrounded, in whole or in part, by regions of therapeutic-substance, delivered during the second treatment. And, optionally, at least one position marker is located within or adjacent to either the resulting site of injury, or the therapeutic-substance delivery site, or a third site or set of sites distinct from the injury and therapeutic-substance sites. Other embodiments of the present invention provide for therapeutic-substance delivery sites surrounded by one or more injury sites.

In use, the device is typically placed inside a patient by urging the device's distal end toward a region of a patient's heart earlier determined to be ischemic or otherwise amenable to the treatment provided by the present invention. The patient's heart is made accessible to the device by open surgery, thoroscopic portals, or intravascularly by inserting a catheter form of the present invention into the body and navigating its distal end toward the area within the patient's body that is sought to be treated. Once positioned near the area of the tissue to be treated, also known as the target tissue, the distal end of the device is manipulated such that the device's thrust axis is perpendicular to the surface of the target tissue. Incorporation of a perpendicularity sensing device, for example, a force contact transducer; as described in U.S. Provisional Patent Application No. 061191,610 by Tom, filed Mar. 23, 2000, or ultrasonic transducer described by Zannelli in U.S. Pat. No. 6,024,703, both of which are entirely incorporated by reference herein, can aid a user in attaining a perpendicular relation between the thrust axis of the tool and the target tissue surface so that tissue penetration by the device is substantially perpendicular to the target tissue surface.

Upon perpendicular placement of the device against a target tissue, the user may activate the device to carry out a sequence of events resulting in the creation of a site of injury surrounded by therapeutic-substance perfused tissue, and, optionally, a position marker. The device may be further controlled by feedback information from the force contact transducer, mentioned above, such that the device may only actuate when the device is urged toward the target tissue with both the appropriate amount and direction of force to optimize device performance.

With the distal end of the device properly placed against the target tissue, the user may then actuate the device to cause the application of the first, second, and optionally, third treatment to the target tissue in the order and fashion dictated by the device's configuration. For example, the first treatment and second treatment may be introduced into the tissue by penetrating needles, where the second treatment needle or needles define lumens that permit substance transfer from a therapeutic-substance reservoir to a therapeutic-substance deposit site created by the puncture of the second treatment needle. The first treatment needle may be an electrode needle for the application of electric energy to cause injury to the target tissue. An electrical circuit is created between the first treatment needle and another electrode located distal to the target tissue. If sufficient electrical current is applied to the electrode, an injury will result in the puncture created by the first treatment needle. Either the first treatment needle or the second treatment needle may be introduced first into the tissue, with the other following while the first is still penetrating, hence combined sequential application, or after withdrawal of the first, hence sequentially. Both first treatment and second treatment needles may also penetrate the tissue simultaneously upon introduction and simultaneously upon withdrawal, or in opposition to one another.

Injury may be introduced by the first treatment needle before, during or after introduction of the second treatment needles, and before, during, or after the delivery of the therapeutic-substance to the puncture region of the introduced second treatment needles. Therapeutic-substance may also be delivered to the site of injury through yet another channel in substance communication with the therapeutic-substance source. Although the first treatment is described as a needle, it need not be limited to such. The present invention provides many alternatives that may be used to induce injury. For example, a needle may be used as an electrical conductor to cause electrical ablation of adjacent tissue. Another example provides for the use of radio frequency electrical abalation as applied through a needle electrode. A needle may further be connected to a mechanical oscillator such as a piezo electric element connected electrically to a driver that causes the needle to vibrate in the ultrasonic range thus sonicating tissue in contact with the needle. Instead of a needle, a fiber optic may deliver light energy sufficient to ablate tissue such as in laser ablation. The light source may be located within the device, or situated outside of the device in optical communication with the device via a fiber optic connection to an external light source. Where electrical current is used to ablate tissue, an external electrical driver, preferably an radio frequency or RF driver, is in electrical communication with the device. Hydraulic energy may be used to ablate tissue where a hydraulic energy generator is in fluid communication with at least one treatment effector defining a lumen for a fluid medium to be expelled from the treatment effector towards the target tissue causing hydraulic ablation or erosion of the target tissue. Preferably the hydraulic energy generator is located external to the device, but in substance communication with the device and at least one of its effectors. Likewise, a pneumatic system may be used to propel small objects into the target tissue to inflict injury. A pneumatic, hydraulic, or mechanical system may be used to actuate a slave force applicator by a master driver located either in a remote region of the device, or external to the device in fluidic or mechanical communication with the device and at least one of the effectors to cause injury when actuated. The invention further provides for depth control for each type of effector where the tissue penetration depth of each effector may be preselected by the user or by design. Besides mechanical and energy type causes of injury, the present invention further provides for chemical or substance caused injury. For example, a mild acid or alcohol may be delivered to injury sites in a target tissue to cause injury.

Therapeutic-substance delivery may be augmented by the application of gentle electrical current to the second treatment needles thus urging the therapeutic-substance into tissue adjacent such second treatment needles by iontophoresis or other electromotive force. Again, a circuit is created between such electrode second treatment needles and a point in the patient distal to the site of the second treatment needle, for example, a remote "grounding pad" or, alternatively, the first treatment needle, or both in combination or opposition (asynchronous).

The third treatment may optionally be applied to the target tissue through the first treatment needle, the second treatment needle, or a third treatment needle, or any combination of the three. The third treatment aims to provide some indication that a region has been visited by the device resulting in treatment. Such indication permits the user to thoroughly cover an area of target tissue sites without either omitting or repeating application to a particular site. The present invention provides for either simultaneous or independent activation of the position marker. Moreover, the ability to use needles from the first, second, or both treatments simplifies the architecture of the device. Another benefit is the ability to inject position marking compounds, for example, contrast agents and fluoroscopic or radio-opaque dyes into the target tissue at a location different than the site of injury, or the site of therapeutic-substance delivery. This feature is beneficial when such marking compounds may interfere with other functions or objectives of the device such as interfering with the therapeutic-substance activity. Injecting marking compounds also widens the array of choices for suitable marking compounds. Contrast agents and radio-opaque dyes, for example, may not be suitable for a stamping method because such agents and dyes may simply wash off the tissue surface without leaving a discernable mark. Injecting such agents and dyes helps to localize such agents and dyes for longer time periods. Alternatively, marking may also occur as a side effect of the first treatment, for example, as when a laser beam is used to cause tissue injury thus leaving a visually perceptible mark. The present invention further provides for position marking, the third treatment, to be done either simultaneously or independent from the actuation of the injury or first treatment, and the therapeutic-substance delivery or second treatment. Independent actuation of the third treatment affords the user the ability to mark off a region with boundaries, for example, by radio-opaque dye, without applying the first and second treatments to such marking areas. The user may then switch to a simultaneous mode to fill in the now defined region with all three treatments thus leaving a position mark at each treatment location between the earlier made boundary marks. Other embodiments of the invention use a stamp to "tattoo" a treatment area with a dye, for example, methylene blue. Fluorescent dyes may also be used and their emission wavelength visualized when the dye is excited.

The invention provides devices having one or more therapeutic-substance or fluid reservoirs in substance communication with one of the treatment effectors, for example, treatment needles, or injection jet nozzles. Therapeutic-substance include, but are not limited to the following. Examples of therapeutic-substances include drugs, genes, viral particles, cells, proteins, nucleic acids, particles, diagnostic agents such as contrast agents, among other things. A therapeutic-substance reservoir may also be in substance communication with a plurality of effectors or one treatment type, or of differing treatment types. Preferably, a therapeutic-substance reservoir is a syringe of the disposable type having standard dimensions, especially at the exit port such as a luer-lock type fitting. A benefit of using a standard syringe is that therapeutic-substance manufacturers may provide pre-loaded syringes for use with the present invention, or otherwise used in related treatment methods. By selecting syringes with different bore diameters a user could vary the range of delivery volume delivered by the device at each treatment site because different volumes would be delivered by different bore diameter syringes even though the plunger on such syringes would be moved inward the same amount. Such control may also be achieved by other mechanisms within the device.

Substance communication between the therapeutic-substance reservoir and the effector or effectors of the present invention may be achieved in many ways. For example, in embodiments having more than one first treatment, or third treatment effectors, there may be a plurality of exit ports emanating from the therapeutic-substance reservoir thus making the reservoir a manifold to the plurality of effectors. Where a therapeutic-substance reservoir has a single exit port, a manifold may be placed in substance communication between the effectors and the therapeutic-substance reservoir. A plurality of effectors may emanate from a manifold, communicating with the manifold which, in turn, is in substance communication with the therapeutic-substance reservoir.

In short, the therapeutic-substance reservoir may also be a manifold, the effector structure may be a manifold, or a separate manifold may be interdisposed between the therapeutic-substance reservoir and the effector structure.

In preferred embodiments, effectors are combined in an effector structure. The effector structure serves to maintain the position of effectors as they are urged into a target tissue. The effector structure may also aid in establishing substance communication between the therapeutic-substance reservoir and each effector. The effector structure may also act as a manifold, as discussed above. In preferred embodiments, the effector is in mechanical communication with a force applicator, operably connected to an actuator so that when the actuator is actuated by the user, the force applicator will apply force to the effector structure to urge at least one treatment, and preferably two or more different treatment effector or effectors toward the target tissue such that those effectors are urged or otherwise advanced into the target tissue. Other embodiments provide for separate force applicators for each type of treatment effector, for example a first force applicator which applies force to a first treatment effector, and a second force applicator which applies force to a second force applicator. Such several force applicators may operate in unison, or individually, or both where the user may select each mode of operation. Force applicators, in conjunction with their respective effector structures and treatment effectors, may further operate in unison, or separately, or both from a therapeutic-substance delivery actuator which causes the therapeutic-substance reservoir to deliver therapeutic-substance via the above described conduits and treatment effectors.

In preferred embodiments, force applicators may comprise a mechanical relation between a user supplied force and an effector structure in mechanical communication with such user supplied force. Other embodiments include motorized force applicators where the user prompts a force supply, such as an electric motor, to supply force to the force applicator. The force supply may exist on-board the device which is preferably hand held, or may exist off board the device in mechanical communication with the device via a mechanical, hydraulic, or pneumatic linkage. The force supply may further be in operable communication with a control structure located-on the device such that a user may activate the force supply by actuating the control structure, or a portion thereof. A force supply may also be used to operate the therapeutic-substance reservoir causing it to deliver therapeutic-substance through its exit port. Embodiments where the force application is provided by the user, operational feedback is further realized to the user by the amount of force required to actuate the device indicating the force necessary to cause the treatment effectors to penetrate or otherwise act upon a tissue for which the device is applied to.

The control structure, in preferred embodiments, includes a single control for actuating the treatment effectors in a preset manner dictated by the device's configuration, and causing the delivery of therapeutic-substance or therapeutic-substances from at least one therapeutic-substance reservoir. Other embodiments provide for separate controls actuating separately different treatment effectors, and separately, or in tandem with a particular type of treatment effector, actuating a therapeutic-substance reservoir. Yet other embodiments provide for combinations of the above described controls. Controls may further be integrated with other components of the device such as the above described force contact transducer to provide an interlock between the force applicator or applicators and their respective controls. The force contact transducer would permit activation of a force applicator, hence a treatment effector, only if the proper axial force or thrust was applied to the tool in the direction of the target tissue and that the thrust axis was essentially perpendicular to the target tissue.

Although the invention has been described with reference to a particular embodiment, it will be appreciated that various changes and modifications may be made without departing from the spirit of the invention.

We claim:

1. A device for treating tissue comprising:
    an elongate shaft having a proximal end, a distal end, and a lumen extending between the proximal end and the distal end;
    at least one injury effector located at the distal end of the elongate shaft, capable of producing an injury at a first tissue location, and having no therapeutic substance delivery capabilities;
    at least one therapeutic substance delivery effector located at the distal end of the elongate shaft, capable of delivering a therapeutic substance to a second tissue location; and
    at least one marking effector located at the distal end of the elongate shaft for creating a position marker at a third tissue location to indicate treated tissue;
    wherein the at least one marking effector is separate from the at least one therapeutic substance delivery effector;
    wherein the at least one injury effector and the at least one marking effector are capable of being sequentially actuated by a control structure;
    wherein the lumen is in substance communication with the at least one therapeutic substance delivery effector and at least a portion of the lumen is configured to receive the therapeutic substance; and
    wherein at least a portion of the at least one injury effector passes through, and is electrically isolated from, the portion of the lumen configured to receive the therapeutic substance.

2. The device of claim 1, wherein the at least one injury effector is capable of inducing a mechanical or energy injury.

3. The device of claim 1, wherein the at least one therapeutic substance delivery effector is in fluid communication with the portion of the lumen configured to receive the therapeutic substance.

4. The device of claim 1, wherein the control structure is operably connected to the elongate shaft for actuation of the device by user activation.

5. The device of claim 4, wherein the at least one injury effector and the at least one therapeutic substance delivery effector are capable of being simultaneously actuated by the control structure.

6. The device of claim 4, wherein the at least one injury effector and the at least one therapeutic substance delivery effector are capable of being sequentially actuated by the control structure.

7. The device of claim 1, wherein the lumen is in fluid communication with a therapeutic substance reservoir.

8. The device of claim 1, wherein the distal end of the elongate shaft is steerable.

9. The device of claim 1, wherein the elongate shaft comprises an endoscope.

10. The device of claim 1, wherein the elongate shaft comprises an open surgical hand held device.

11. The device of claim 1, wherein the at least one injury effector has a first exposed length and the at least one therapeutic-substance delivery effector has a second exposed length, and wherein the first exposed length is greater than the second exposed length.

12. The device of claim 1, wherein a plurality of therapeutic-substance delivery effectors are disposed radially around the at least one injury effector.

13. The device of claim 1, wherein the third tissue location is different from the first tissue location and the second tissue location.

14. The device of claim 1, wherein the second tissue location is below an outer surface of the tissue.

15. A device for treating tissue comprising:
an elongate shaft having a proximal end, a distal end, and a lumen extending between the proximal end and the distal end;
at least one injury effector located at the distal end of the elongate shaft, capable of producing an injury at a first tissue location, and having no therapeutic substance delivery capabilities;
at least one therapeutic substance delivery effector located at the distal end of the elongate shaft, capable of delivering a therapeutic substance to a second tissue location; and
at least one marking effector located at the distal end of the elongate shaft for creating a position marker at a third tissue location to indicate treated tissue;
wherein the at least one marking effector is separate from the at least one injury effector and the at least one therapeutic substance delivery effector;
wherein the lumen is in substance communication with the at least one therapeutic substance delivery effector and at least a portion of the lumen is configured to receive the therapeutic substance; and
wherein at least a portion of the at least one injury effector passes through, and is electrically isolated from, the portion of the lumen configured to receive the therapeutic substance.

16. The device of claim 15, wherein the elongate shaft comprises an endoscope.

17. The device of claim 15, wherein the at least one injury effector has a first exposed length and the at least one therapeutic-substance delivery effector has a second exposed length, and wherein the first exposed length is greater than the second exposed length.

18. The device of claim 15, wherein the third tissue location is different from the first tissue location and the second tissue location.

19. The device of claim 15, wherein the at least one therapeutic substance delivery effector and the at least one marking effector are capable of being sequentially actuated by a control structure.

20. The device of claim 15, wherein the at least one injury effector and the at least one therapeutic substance delivery effector are capable of being sequentially actuated by a control structure.

* * * * *